US010239902B2

(12) United States Patent
Park et al.

(10) Patent No.: US 10,239,902 B2
(45) Date of Patent: Mar. 26, 2019

(54) STABLE PEPTIDE-CONJUGATED ASCORBIC ACID DERIVATIVE, METHOD FOR PREPARING SAME, AND COSMETIC COMPOSITION COMPRISING SAME

(71) Applicant: CELLTRION INC., Incheon (KR)

(72) Inventors: Young Jun Park, Gyeonggi-do (KR); Jung Yun Kim, Incheon (KR); Jin Kyo Jeong, Seoul (KR); Hyeong Mi Kim, Gyeonggi-do (KR); Eun Joo Cho, Daegu (KR); Joo Hyuck Lim, Incheon (KR); Hyun Nam Song, Gyeonggi-do (KR); Seon Kyung Park, Incheon (KR); Won Kang Moon, Seoul (KR); Shin Jae Chang, Incheon (KR); Seung Suh Hong, Seoul (KR)

(73) Assignee: CELLTRION INC., Incheon (KR)

(*) Notice: Subject to any disclaimer, the term of this patent is extended or adjusted under 35 U.S.C. 154(b) by 167 days.

(21) Appl. No.: 15/606,628

(22) Filed: May 26, 2017

(65) Prior Publication Data
US 2017/0258931 A1  Sep. 14, 2017

Related U.S. Application Data

(63) Continuation of application No. PCT/KR2015/011218, filed on Oct. 22, 2015.

(30) Foreign Application Priority Data

Nov. 27, 2014 (KR) .................. 10-2014-0167350

(51) Int. Cl.
C07F 9/6584 (2006.01)
A61Q 19/00 (2006.01)
C07D 307/62 (2006.01)
A61K 8/67 (2006.01)
A61Q 19/02 (2006.01)
A61Q 19/08 (2006.01)
C07F 9/655 (2006.01)
A61K 9/00 (2006.01)
A61K 47/14 (2017.01)
A61K 9/06 (2006.01)
C07K 5/00 (2006.01)
C07K 5/09 (2006.01)
A61K 47/64 (2017.01)
A61K 8/00 (2006.01)
A61K 51/08 (2006.01)
C07H 11/04 (2006.01)
A61K 47/42 (2017.01)

(52) U.S. Cl.
CPC .......... *C07F 9/65846* (2013.01); *A61K 8/676* (2013.01); *A61K 9/0014* (2013.01); *A61K 9/06* (2013.01); *A61K 47/14* (2013.01); *A61K 47/64* (2017.08); *A61Q 19/00* (2013.01); *A61Q 19/02* (2013.01); *A61Q 19/08* (2013.01); *C07D 307/62* (2013.01); *C07F 9/65515* (2013.01); *C07K 5/00* (2013.01); *C07K 5/0815* (2013.01); *C07K 5/0817* (2013.01); *A61K 8/00* (2013.01); *A61K 47/42* (2013.01); *A61K 51/08* (2013.01); *C07H 11/04* (2013.01)

(58) Field of Classification Search
CPC ............ C07F 9/65846; C07F 9/65515; C07K 5/0815; C07K 5/0817; C07K 5/00; C07D 307/62; A61Q 19/00; A61Q 19/08; A61Q 19/02; A61K 51/08; A61K 8/00; A61K 47/42; A61K 47/64; A61K 47/14; A61K 9/0014; A61K 8/676; A61K 9/06; C07H 11/04
See application file for complete search history.

(56) References Cited

U.S. PATENT DOCUMENTS 5,409,693 A   4/1995   Perricone

FOREIGN PATENT DOCUMENTS

| JP | H04182492 A | 6/1992 |
| JP | H11001486 A | 1/1999 |
| JP | 2001270816 A | 10/2001 |
| JP | 2008222970 A | 9/2008 |
| KR | 100459679 B1 | 12/2004 |
| WO | 2004028484 A1 | 4/2004 |
| WO | 2007094030 A1 | 8/2007 |

OTHER PUBLICATIONS

Office Action issued in corresponding Japanese Application No. 2017-527922 dated Jul. 9, 2018, and English translation thereof (6 pages).

Kang, Hak Hee et al. "Synthesis of L-Ascorbic Acid Derivative Including 3-Aminopropane Phosphoric Acid as a Novel Whitening Agent" Bull. Korean Chem. Soc. 2003, vol. 24, No. 8, pp. 1169-1171 (3 pages).

*Primary Examiner* — Robert S Cabral
(74) *Attorney, Agent, or Firm* — Osha Liang LLP

(57) ABSTRACT

The present invention provides a stable peptide-conjugated, ascorbic acid derivative, a method for preparing the same, and a cosmetic composition comprising the same as an active ingredient. The stable peptide-conjugated ascorbic acid derivative of the present invention has both the effect of whitening the skin by inhibiting melanin production and the effect of reducing skin wrinkles by activating collagen production, and may be used in a cosmetic composition.

9 Claims, No Drawings

STABLE PEPTIDE-CONJUGATED ASCORBIC ACID DERIVATIVE, METHOD FOR PREPARING SAME, AND COSMETIC COMPOSITION COMPRISING SAME

TECHNICAL FIELD

The present invention relates to a stable peptide-conjugated ascorbic acid derivative exhibiting an excellent wrinkle-reducing effect and an excellent whitening effect, a method for preparing the same, and a cosmetic composition comprising the same as an active ingredient.

BACKGROUND ART

Generally, ascorbic acid acts as a reducing agent, a collagen synthesis promoter or an antioxidant, stimulates iron absorption in the small intestines, and is involved in carnitine biosynthesis and immunity. It is known that, when the body is deficient in ascorbic acid, scurvy, the abnormalities in connective tissue caused by abnormalities in collagen synthesis, bone pain, bone fracture, diarrhea, etc., may occur, and when an excessive amount of ascorbic acid exists in the body, gastrointestinal disorders, including nausea, abdominal pain, diarrhea and the like, may occur. In particular, the excellent antioxidant effect of ascorbic acid is known to inhibit melanin production in the skin, thereby preventing abnormal pigmentations such as freckles, and thus ascorbic acid is attracting attention as a material for skin external use.

Although ascorbic acid exhibits various effects as described above, it has problems in that it is mostly destroyed when being heated in air, is unstable against alkali, and is easily oxidized in an aqueous solution to lose such effects. Thus, in order to overcome this instability of ascorbic acid, various ascorbic acid derivatives have been developed.

Previously developed ascorbic acid derivatives are as follows. First, there are derivatives such as phosphorylated ascorbic acid or metal salts thereof. Such derivatives are easily converted to an L-ascorbic acid form available in the human body, compared to other derivatives, but has a disadvantage in that they are difficult to absorb into the skin, because they have negative charges. Second, a variety of fatty acid-conjugated derivatives are known, including ascorbyl palmitate, ascorbyl laurate, ascorbyl stearate, etc. Among these derivatives, ascorbyl-6-palmitate is most widely used (see U.S. Pat. No. 5,409,693). These derivative compounds are absorbed into the skin, but have a disadvantage in that they are difficult to convert into an L-ascorbic acid form. Third, collagen-producing peptide-conjugated ascorbic acid derivatives are known in which a succinoyl group is linked to the hydroxyl group at carbon 5 or carbon 6 of ascorbic acid by an ester bond and the collagen-producing peptide is linked by an amide bond (see Korean Patent No. KR 10-0459679]. These derivatives show excellent efficacy compared to ascorbic acid, but have the disadvantage of having poor stability.

As described above, almost all ascorbic acid derivatives developed to date were not improved in terms of efficacy or stability compared to pure ascorbic acid, and peptide-conjugated ascorbic acid derivatives mostly have aimed to enhance only the whitening effect of ascorbic acid. Thus, the wide use of these derivatives for cosmetic applications is limited.

DISCLOSURE

Technical Problem

Accordingly, the present inventors have made extensive efforts to develop an ascorbic acid derivative having both a wrinkle-reducing effect and a whitening effect while overcoming the problems of conventional ascorbic acid derivatives. As a result, the present inventors have found that, when a peptide compound having 2 to 5 units is conjugated to an ascorbic acid aminopropanol phosphoric acid diester compound, a stable ascorbic acid derivative having both a wrinkle-reducing effect and a whitening effect can be obtained, thereby completing the present invention.

Therefore, it is an object of the present invention to provide a peptide-conjugated ascorbic acid derivative represented by the following formula I or a cosmetically acceptable salt thereof.

Another object of the present invention is to provide a method for preparing a peptide-conjugated ascorbic acid derivative represented by the following formula I or a cosmetically acceptable salt thereof.

Still another object of the present invention is to provide a cosmetic composition comprising, as an active ingredient, a peptide-conjugated ascorbic acid derivative represented by the following formula I or a cosmetically acceptable salt thereof, and the use thereof for skin wrinkle reduction and whitening.

Technical Solution

The present invention is directed to a peptide-conjugated ascorbic acid derivative represented by the following formula I or a cosmetically acceptable salt thereof:

Formula I

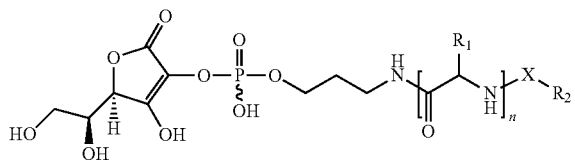

wherein

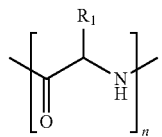

represents a peptide in which the same or different amino acid residues selected from among natural or non-natural amino acid residues are bonded by amide bonds;

$R_1$ represents side chains of the amino acid residues;

$R_1'$ is equal to $R_1$ or is $R_1$ in which amino group or carboxyl group is protected;

X is hydrogen or carbonyl (C=O);

$R_2$ is null when X is hydrogen, or $R_2$ is palmityl, lauryl or stearyl when X is carbonyl; and n is an integer ranging from 2 to 5.

Preferably,

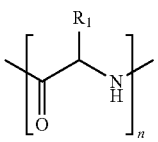

represents a peptide in which the same or different amino acid residues selected from among glycine, alanine, serine, threonine, cysteine, valine, leucine, isoleucine, proline, hydroxyproline, lysine, phenylalanine, methionine, tyrosine, tryptophan, asparagine, glutamine, histidine, aspartic acid, glutamic acid, and arginine are bonded by amide bonds; $R_1$ represents side chains of the amino acid residues; and n is an integer ranging from 3 to 5.

More preferably,

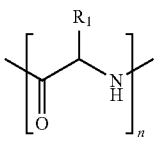

represents a peptide in which the same or different amino acid residues selected from among valine, lysine, glycine, arginine, aspartic acid, threonine, and serine are bonded by amide bonds; $R_1$ represents side chains of the amino acid residues; and n is an integer ranging from 3 to 5.

Even more preferably,

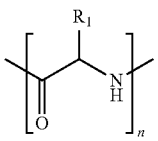

represents lysine-valine-lysine or arginine-glycine-aspartic acid.

As used herein, the term "natural amino acids" refers to α-amino acids selected from the group consisting of alanine, valine, leucine, isoleucine, proline, phenylalanine, tryptophan, methionine, glycerin, serine, threonine, cysteine, tyrosione, asparagine, glutamine, lysine, arginine, histidine, aspartic acid and glutamic acid.

As used herein, the term "non-natural amino acids" refers to amino acids which are not encoded by a nucleic acid codon, and examples of the non-natural amino acids include, but are not limited to, D-isomers of the natural α-amino acids as described above; Aib (aminobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutyric acid), α-aminopimelic acid, IMSA (trimethylsilyl-Ala), alle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), etc.; cyclic amino acids; N α-alkylated amino acids, for example, MeGly (Nα methylglycine), EtGly (Nα ethylglycine) and EtAsn (Nα ethylasparagine); and amino acids having two side chain substituents on α-carbon.

The peptide-conjugated ascorbic acid derivative according to the present invention is selected from the group consisting of the following compounds:
(6S,9S,12S)-6,12-bis(4-aminobutyl)-9-isopropyl-5,8,11,14-tetraoxo-4,7,10,13-tetraazanonacosyl (5-((S)-1,2-dihydroxyethyl)-4-hydroxy-2-oxo-2,5-dihydrofuran-3-yl) hydrogen phosphate (I-1); and
(3S)-3-(2-((S)-2-amino-5-((diaminomethylene)amino)pentanamido)acetamido)-4-((3-((((5-((S)-1,2-dihydroxyethyl)-4-hydroxy-2-oxo-2,5-dihydrofuran-3-yl)oxy)(hydroxy)phosphoryl)oxy)propyl)amino)-4-oxobutanoic acid (I-2).

In the present invention, "cosmetically acceptable salt" include, but are not limited to, all nontoxic inorganic acid salts and organic acid salts, for example, hydrochloric acid salts, sulfuric acid salts, nitric acid salts, phosphoric acid salts, acetic acid salts, trifluoroacetic acid salts, benzenesulfonic acid salts, citric acid salts, etc.

The present invention is also directed to a method for preparing the peptide-conjugated ascorbic acid derivative represented by formula I. The preparation method of the present invention comprises a step of subjecting an ascorbic acid aminopropanol phosphoric acid diester compound of the following formula II to a condensation reaction with a peptide compound of the following formula IV with 2 to 5 units, and then subjecting the product to a deprotection reaction if a protecting group is present in the product:

Formula II

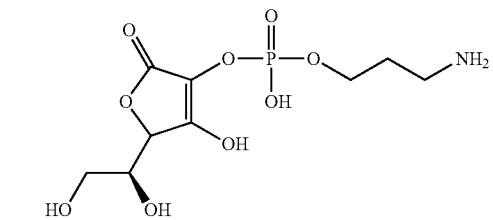

Formula IV

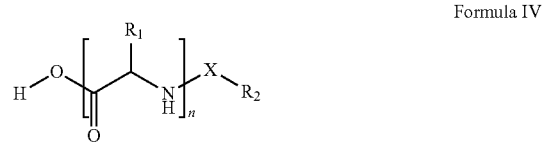

wherein

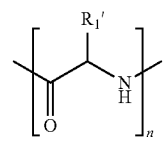

represents a peptide in which the same or different amino acid residues selected from among natural or non-natural amino acid residues are bonded by amide bonds;
$R_1$ represents side chains of the amino acid residues;
$R_1'$ is equal to $R_1$ or is $R_1$ in which amino group or carboxyl group is protected;
X is hydrogen or carbonyl (C=O);
$R_2$ is null when X is hydrogen, or $R_2$ is palmityl, lauryl or stearyl when X is carbonyl; and
n is an integer ranging from 2 to 5.

As the amino protecting group of the compound of formula IV, t-butoxycarbonyl (t-Boc), carbobenzyloxy (Cbz), 9-fluorenylmethoxycarbonyl (Fmoc) or the like may be used, but is not limited thereto. Furthermore, deprotection of the amino protecting group of the compound of formula IV may be performed using hydrochloric acid or trifluoroacetic acid, but is not limited thereto.

As the carboxyl protecting group of the compound of formula IV, methyl, ethyl, t-butyl, 2,2,2-trichloroethyl or the like may be used, but is not limited thereto. Furthermore, deprotection of the carboxyl protecting group of the compound of formula IV may be performed using lithium hydroxide or trifluoroacetic acid, but is not limited thereto.

The condensation reaction may be performed in the presence of a condensing agent. Examples of a condensing agent that may be used in the condensation reaction include, but are not limited to, dicyclohexylcarbodiimide (DCC), diphenylphosphoryl azide (DPPA), diethyl cyanophosphonate (DEPC), benzotriazol-1-yl-oxy-tris(dimethylamino) phosphonium hexafluorophosphate (BOP reagent) and the like. In the condensation reaction, an organic base such as triethylamine or diisopropylethylamine (DIPEA) may, if necessary, be used together with the condensing agent, and an activator such as 4-(dimethylamino)pyridine (DMAP) or N-hydroxysuccinimide (HOSu) may, if necessary, be used.

Examples of a solvent that may be used in the condensation reaction include halogenated aliphatic hydrocarbons such as chloroform and dichloromethane, ethyl acetate, tetrahydrofuran (THF), dimethylformamide (DMF), acetonitrile, 1,4-dioxane, methanol, etc. The condensation reaction may be performed at a temperature of −10° C. to 50° C., preferably 0° C. to 25° C.

The compound of formula II may be synthesized according to a known method (see Bull. Korean Chem. Soc., 2003, Vol. 24, No. 8, pp 1169-1171), or is a commercially available product.

In the compound of formula IV, the peptide (where $R_2$ is null) or the fatty acid-peptide (where $R_2$ is palmityl, lauryl or stearyl) may be a peptide synthesized using a solid phase synthesis method or a fatty acid-peptide synthesized by polymerizing the synthesized peptide with a fatty acid, or may be a commercially available product.

Hereinafter, the method for preparing the peptide-conjugated ascorbic acid derivative of formula I according to the present invention will be described in detail with reference to the following reaction scheme I. The method shown in the following reaction scheme I is merely representative of possible preparation methods, and the sequence of unit operations, reagents, reaction conditions, etc., which are shown in the following reaction scheme I, may be properly modified, if necessary.

Reaction Scheme I

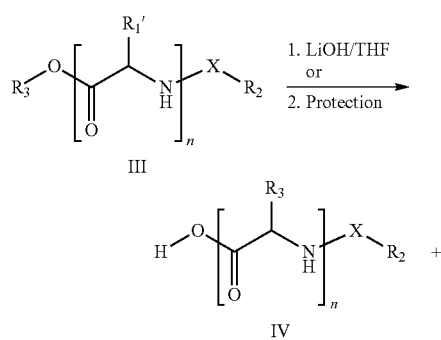

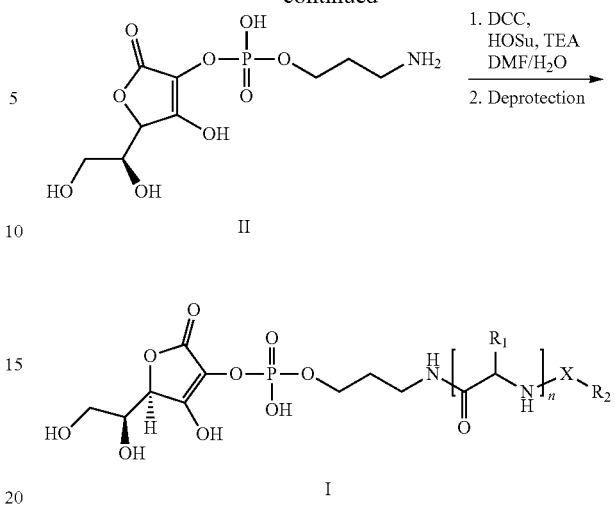

wherein

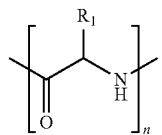

represents a peptide in which the same or different amino acid residues selected from among natural or non-natural amino acid residues are bonded by amide bonds;

$R_1$ represents side chains of the amino acid residues;

X is hydrogen or carbonyl (C=O);

$R_2$ is null when X is hydrogen, or $R_2$ is palmityl, lauryl or stearyl when X is carbonyl;

$R_3$ is hydrogen, methyl, ethyl, t-butyl, or 2,2,2-trichloroethyl; and n is an integer ranging from 2 to 5.

The preparation method according to the present invention comprises the steps of:

(i) either protecting the compound of formula III with an amino protecting group such as t-butoxycarbonyl (t-Boc) and a carboxyl protecting group such as t-butyl to obtain an compound of formula IV in which amino group and carboxyl group are protected, or deprotecting the C-terminal carboxyl group of the compound of formula III with a base such as lithium hydroxide to obtain a compound of formula IV; and (ii) subjecting the compound of formula IV to a condensation reaction with the compound of formula II (3-aminopropyl (5-((S)-1,2-dihydroxyethyl)-4-hydroxy-2-oxo-2,5-dihydrofuran-3-yl)hydrogen phosphate) in the presence of a condensing agent such as dicyclohexylcarbodiimide (DCC), and deprotecting the amino group and carboxyl group of the amino acid side chain with hydrochloric acid or trifluoroacetic acid, thereby obtaining the compound of formula I.

If the compound of formula III does not need to be subjected to the protecting or deprotecting step (i) of the preparation method, the compound of formula I may be synthesized by performing step (ii) without performing step (i).

The peptide-conjugated ascorbic acid derivative of the present invention, prepared according to the above-described method, is stable and also exhibits both an excellent wrinkle-reducing effect and an excellent whitening effect (see Experimental Examples 1, 2 and 3 below).

The present invention is also directed to a cosmetic composition, comprising: the peptide-conjugated ascorbic acid derivative of formula I or a cosmetically acceptable salt thereof; and a cosmetically acceptable base. The cosmetic composition of the present invention particularly has both a skin wrinkle-reducing effect and a skin whitening effect.

The cosmetic composition of the present invention comprises, based on the total weight of the cosmetic composition, 0.0001-2 wt %, preferably 0.01-0.20 wt % of the compound of formula I as an active ingredient.

The formulation of the cosmetic composition according to the present invention is not particularly limited, and the cosmetic composition of the present invention may comprise conventional cosmetic composition components known in the art depending on the formulation to be prepared. The cosmetic composition of the present invention may be prepared as formulations such as lotion, emulsion, nourishing cream, pack, beauty liquid, essence or the like, and may further comprise one or more components selected from among oil, water, surfactants, moisturizing agents, lower alcohols, thickeners, chelating agents, pigments, preservatives, fragrances and the like, depending on the formulation to be prepared. Furthermore, in view of the fact that the major cause of melanin formation is UV rays, the cosmetic composition of the present invention may comprise a UV blocking agent, a light scattering agent or the like. However, the formulation and components of the cosmetic composition are not limited to the above-described contents.

Advantageous Effects

The peptide-conjugated ascorbic acid derivative according to the present invention is a novel synthetic compound and exhibits both the effect of whitening the skin by inhibiting melanin formation and the effect of reducing skin wrinkles by activating collagen production, thereby may be advantageously used in cosmetic compositions.

MODE FOR INVENTION

Hereinafter, the present invention will be described in further detail with reference to preparation examples and examples. It will be obvious to those skilled in the art that these preparation examples and examples are for illustrative purposes only and are not intended to limit the scope of the present invention.

Preparation Example 1

Preparation of Compound of Formula IV in which Amino Group (—NH$_2$)— and Carboxyl Group (—COOH)— are Protected Preparation Example 1-1

(10S,13S,16S)-16-(4-((t-butoxycarbonyl)amino)butyl)-13-isopropyl-2,2-dimethyl-4,11,14-trioxo-10-palmitamido-3-oxa-5,12,15-triazaheptadecan-17-oate (IV-1)

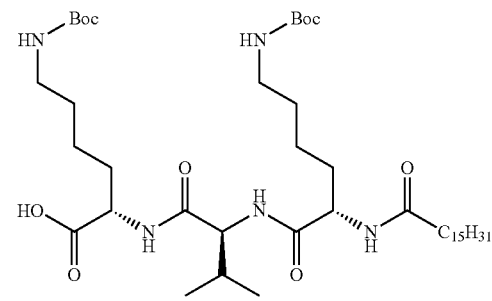

Palmitoyl tripeptide-5 (Pal-KVK) (30.6 g, 50 mmol) was dissolved in 100 mL of methanol and 50 mL of triethylamine. The reaction solution was cooled to 0° C., and di-t-butyl dicarbonate (29 mL, 125 mmol) was added thereto, followed by stirring at room temperature for 18 hours. After completion of the reaction, the reaction solution was concentrated under reduced pressure to remove the solvent, and a saturated sodium hydrogen carbonate solution (150 mL) was added to the residue which was then washed twice with diethyl ether (150 mL). The aqueous layer was adjusted to pH 2 by addition of 1M aqueous sodium hydrogen sulfate solution (200 mL) and extracted three times with ethyl acetate (300 mL), and the organic layer was washed sequentially with distilled water (300 mL) and saturated aqueous sodium chloride solution (300 mL), and then dried with anhydrous sodium sulfate and concentrated under reduced pressure to afford the title compound (34 g, 84%).

ES-MS m/z: 812 [M+H]$^+$
$^1$H NMR (400 MHz, CDCl$_3$) δ 0.89 (m, 3H), 0.97 (m, 6H), 1.28-1.43 (m, 48H), 1.59-1.99 (m, 8H), 2.06 (m, 1H), 2.24 (brt, J=7.2 Hz, 2H), 3.02 (m, 4H), 4.20 (d, J=7.2 Hz, 1H), 4.37 (m, 2H).

Preparation Example 1-2

(11S,17S)-17-(2-(t-butoxy)-2-oxoethyl)-6,11-bis((t-butoxycarbonyl)amino)-2,2-dimethyl-4,12,15-trioxo-3-oxa-5,7,13,16-tetraazaoctade-6-cen-18-oate (IV-2)

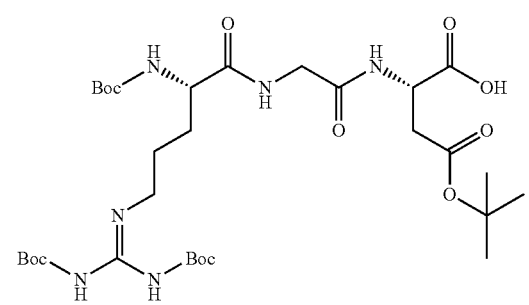 [SMILES: CC(C)(C)OC(=O)C[C@H](NC(=O)CNC(=O)[C@H](CCCN=C(NC(=O)OC(C)(C)C)NC(=O)OC(C)(C)C)NC(=O)OC(C)(C)C)C(=O)O]

N-carbobenzoxyglycine (Z-Gly-OH) (11.48 g, 54.8 mmol) and L-aspartic acid 4-t-butyl-1-methyl ester hydrochloride (13.14 g, 54.8 mmol) were dissolved in tetrahydrofuran (275 ml), and then cooled to 0° C. To the reaction solution, 1-hydroxybenzotriazole hydrate (HOBt) (8.90 g, 65.8 mmol) and 1-(3-dimethylaminopropyl)-3-ethylcarbodiimide hydrochloride (EDC.HCl) (11.31 g, 65.8 mmol) were added, and triethylamine (23.1 mL, 164.6 mmol) was added dropwise. The reaction solution was stirred at 0° C. for 30 minutes, and then stirred at room temperature for 16 hours. After completion of the reaction, water (200 mL) was added to the reaction mixture solution which was then washed three times with ethyl acetate (100 mL). Next, the organic layers were combined, washed with saturated aqueous sodium chloride solution (200 mL), dried with anhydrous sodium sulfate, and then concentrated under reduced pressure. The residue was purified by column chromatography to afford (S)-4-t-butyl 1-methyl 2-(2-(((benzyloxy)carbonyl)amino)acetamido)succinate (16.0 g, 74%).

ES-MS m/z: 395 [M+H]$^+$, 417 [M+Na]$^+$ $^1$H NMR (400 MHz, DMSO-d6) δ 1.41 (s, 9H), 2.68-2.83 (m, 2H), 3.61 (s, 3H), 3.62 (s, 3H), 3.62-3.64 (m, 2H), 4.64-4.69 (m, 1H), 5.03 (s, 2H), 7.31-7.39 (m, 5H), 7.46 (t, 1H), 8.35 (d, 1H).

The obtained compound (16.0 g, 40.57 mmol) was dissolved in methanol (200 mL), and 10% palladium carbon (2.02 g) was added thereto, followed by stirring at room temperature for 3 hours in a hydrogen atmosphere. After completion of the reaction, the reaction mixture was filtered through celite, washed several times with methanol, and then concentrated under reduced pressure to remove the solvent, thereby obtaining (S)-4-t-butyl 1-methyl 2-(2-aminoacetamido)succinate (8.04 g, 91%) as a white solid.

ES-MS m/z: 261 [M+H]$^+$, 283 [M+Na]$^+$ $^1$H NMR (400 MHz, DMSO-d$_6$) δ 1.41 (s, 9H), 2.64-2.78 (m, 2H), 3.47 (s, 3H), 3.62 (s, 3H), 3.65-3.77 (m, 2H), 4.10-4.12 (m, 1H), 8.10 (s, 1H).

(S)-4-t-butyl 1-methyl 2-(2-aminoacetamido)succinate (8.04 g, 30.89 mmol) and N$_α$Boc-N$_δ$Cbz-L-ornithine (13.5 g, 38.8 mmol) were dissolved in tetrahydrofuran (185 mL) and cooled to 0° C. To the reaction solution, 1-hydroxybenzotriazole hydrate (HOBt) (5.98 g, 44.2 mmol) and 1-(3-dimethylaminopropyl)-3-ethylcarbodiimide hydrochloride (EDC.HCl) (7.6 g, 44.2 mmol) were added, and triethylamine (11.39 mL, 84.1 mmol) was added dropwise. The reaction mixture was stirred at 0° C. for 30 minutes, and then stirred at room temperature for 16 hours. After completion of the reaction, water (150 mL) was added to the reaction mixture solution which was then washed twice with ethyl acetate (100 mL), dried with anhydrous sodium sulfate, and concentrated under reduced pressure. The residue was purified by column chromatography to afford (S)-4-t-butyl 1-methyl 2-(2-((S)-5-(((benzyloxy)carbonyl)amino)-2-((t-butoxycarbonyl)amino)pentaamido)acetamido)succinate (9.76 g, 47%) as a white solid.

ES-MS m/z: 609 [M+H]$^+$, 631 [M+Na]$^+$ $^1$H NMR (400 MHz, CDCl$_3$) δ 1.44 (s, 18H), 1.58-1.66 (m, 4H), 1.82-1.92 (m, 1H), 2.81-2.87 (m, 1H), 2.96-3.01 (m, 1H), 3.15-3.39 (m, 2H), 3.67 (s, 3H), 3.72 (s, 3H), 3.94 (m, 2H), 4.25 (m, 1H), 4.83 (m, 1H), 5.08 (s, 2H), 5.13 (m, 2H), 7.00 (m, 2H), 7.32-7.35 (m, 5H).

The obtained compound (9.76 g, 17.2 mmol) was dissolved in methanol (85 mL), and 10% palladium carbon (0.86 g) was added thereto, followed by stirring at room temperature for 3 hours in a hydrogen atmosphere. After completion of the reaction, the reaction mixture was filtered through celite, washed several times with methanol, and then concentrated under reduced pressure to remove the solvent, thereby obtaining (S)-4-t-butyl 1-methyl 2-(2-((S)-5-amino-2-((t-butoxycarbonyl)amino)pentaamido)acetamido)succinate (7.45 g, 99%) as a white solid.

ES-MS m/z: 475 [M+H]$^+$, 497 [M+Na]$^+$ $^1$H NMR (400 MHz, CDCl$_3$) δ 1.44 (s, 18H), 1.52-1.61 (m, 2H), 1.72-1.77 (m, 1H), 1.76-1.87 (m, 1H), 2.20 (brd, 4H), 2.75 (m, 1H), 2.79-2.85 (m, 1H), 2.98-3.03 (m, 1H), 3.69 (s, 3H), 3.75 (s, 3H), 3.94 (m, 2H), 4.20 (m, 1H), 4.85 (m, 1H), 5.84 (m, 1H), 7.16 (m, 1H), 7.54 (m, 1H).

(S)-4-t-butyl 1-methyl 2-(2-((S)-5-amino-2-((t-butoxycarbonyl)amino)pentamido)acetamido)succinate (7.45 g, 17.2 mmol) was dissolved in dichloromethane (85 mL), and 1,3-di-Boc-2-(trifluoromethylsulfonyl)guanidine (7.08 g, 18.1 mmol) and triethylamine (2.5 mL, 18.1 mmol) were added thereto, followed by stirring at room temperature for 16 hours. After completion of the reaction, water (85 mL) was added to the reaction mixture solution which was then washed twice with dichloromethane (50 mL), dried with anhydrous sodium sulfate, and then concentrated under reduced pressure. The residue was purified by column chromatography to afford (S)-4-t-butyl 1-methyl 2-((S)-6,11-bis((t-butoxycarbonyl)amino)-2,2-dimethyl-4,12-dioxo-3-oxa-5,7,13-triazapentade-6-cenamido)succinate (11.43 g, 98%) as a white solid.

ES-MS m/z: 718 [M+H]$^+$, 740 [M+Na]$^+$ $^1$H NMR (400 MHz, CDCl$_3$) δ 1.44 (s, 18H), 1.48 (s, 18H), 1.64-1.72 (m, 4H), 1.87 (m, 1H), 2.81-2.86 (m, 1H), 2.96-3.01 (m, 1H), 3.30 (m, 1H), 3.48 (m, 1H), 3.68 (s, 3H), 3.74 (s, 3H), 3.96 (m, 2H), 4.24 (m, 1H), 4.85 (m, 1H), 5.54 (m, 1H), 7.04 (m, 1H), 7.10 (m, 1H), 8.41 (m, 1H), 11.43 (m, 1H)

(S)-4-t-butyl 1-methyl 2-((S)-6,11-bis((t-butoxycarbonyl)amino)-2,2-dimethyl-4,12-dioxo-3-oxa-5,7,13-triazapentade-6-cenamido)succinate (11.43 g, 16.9 mmol) was dissolved in tetrahydrofuran (127 mL) and cooled to 0° C., and 1M lithium hydroxide solution (45 mL) was added thereto, followed by stirring at room temperature for 16 hours. After completion of the reaction, the reaction solution was cooled to 0° C., adjusted to pH 2 by 1 M HCl aqueous solution, and extracted twice with ethyl acetate (80 mL). The organic layers were combined, washed with saturated aqueous sodium chloride solution (100 mL), dried with anhydrous sodium sulfate, and then concentrated under reduced pressure, thereby obtaining the title compound (8.96 g, 82%) as a white solid.

ES-MS m/z: 703 [M+H]$^+$, 725 [M+Na]$^+$ $^1$H NMR (400 MHz, CDCl$_3$) δ 1.28 (t, 1H), 1.42 (s, 18H), 1.48 (s, 9H), 1.49 (s, 9H), 1.62-1.65 (m, 3H), 1.85 (m, 1H), 2.81-2.85 (m, 1H), 2.99-3.04 (m, 1H), 3.40 (m, 1H), 3.85 (m, 1H), 4.13 (m, 1H), 4.76 (m, 1H), 5.24 (m, 1H), 5.85 (m, 1H), 5.82 (m, 1H), 7.71 (m, 2H), 8.67 (m, 1H).

Examples: Preparation of Compound of Formula I

Example 1: (6S,9S,12S)-6,12-bis(4-aminobutyl)-9-isopropyl-5,8,11,14-tetraoxo-4,7,10,13-tetraazanonacosyl 5-((S)-1,2-dihydroxyethyl)-4-hydroxy-2-oxo-2,5-hydrofuran-3-yl)hydrogen phosphate hydrochloride (I-1)

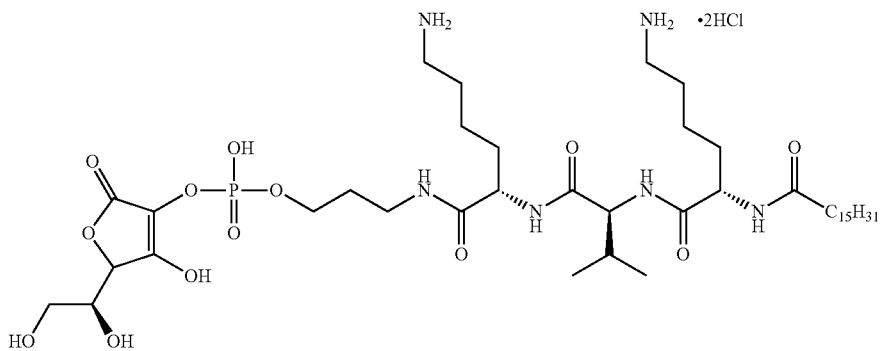

The compound IV-1 in which amino group is protected (31.2 g, 38.4 mmol) obtained in Preparation Example 1-1 was dissolved in dimethylformamide (250 mL), and N,N'-dicyclohexylcarbodiimide (DCC) (9.5 g, 46.1 mmol) and N-hydroxysuccinimide (5.3 g, 46.1 mmol) were added thereto, followed by undergoing the reaction at room temperature for 3 hours. After the reaction, N,N'-dicyclohexylurea produced as a by-product was removed by filtration under reduced pressure. To the remaining filtrate, 3-aminopropyl(5-((S)-1,2-dihydroxyethyl)-4-hydroxy-2-oxo-2,5-dihydrofuran-3-yl)hydrogen phosphate (Vitagen, 13.2 g, 42.2 mmol) of formula II and diisopropylethylamine (13.5 mL, 77 mmol) were added and stirred at room temperature for 20 hours. After completion of the reaction, the reaction solution was concentrated under reduced pressure to remove the solvent. The residue was recrystallized by sequential addition of MeOH, dichloromethane and isopropyl ether, and filtered to obtain an compound (47 g, 112%) of formula I-1 in which amino group is protected.

ES-MS m/z: 1107 [M+H]$^+$ $^1$H NMR (400 MHz, CD$_3$OD) δ 0.96 (m, 3H), 1.01 (m, 6H), 1.35-1.55 (m, 48H), 1.65-1.88 (m, 10H), 2.14 (m, 1H), 2.30 (brt, J=7.2 Hz, 2H), 3.09 (m, 4H), 3.28 (m, 2H), 3.73-3.82 (m, 3H), 4.00 (m, 1H), 4.06 (m, 2H), 4.22 (d, J=6.8 Hz, 1H), 4.37 (m, 2H), 4.86-5.01 (m, 1H).

The obtained compound (47 g, 37.9 mmol) of formula I-1 in which amino group is protected was dissolved in 1,4-dioxane (160 mL), and 4 M hydrochloric acid in 1,4-dioxane solution (110 mL, 440 mmol) was added thereto, followed by stirring at room temperature for 15 hours. After completion of the reaction, the reaction solution was concentrated under reduced pressure to remove the solvent. Acetonitrile (600 mL) was added to the residue, and the formed solid was filtered to afford the title compound (33.0 g, 89%).

ES-MS m/z: 907 [M+H]$^+$ $^1$H NMR (400 MHz, CD$_3$OD) δ 0.90 (m, 3H), 0.92 (d, J=6.4 Hz, 6H), 1.28-1.39 (m, 26H), 1.44-1.88 (m, 14H), 2.12 (m, 1H), 2.25 (brt, J=7.6 Hz, 2H), 2.96 (m, 4H), 3.24-3.35 (m, 2H), 3.68 (m, 3H), 3.95-3.99 (td, J=1.6, 6.8 Hz, 1H), 4.08-4.15 (m, 3H), 4.29 (m, 1H), 4.37 (m, 1H), 4.93 (m, 1H).

Example 2: (3S)-3-(2-((5)-2-amino-5-((diaminomethylene)amino)pentanamido)acetamido)-4-((3-((((5-((S)-1,2-dihydroxyethyl)-4-hydroxy-2-oxo-2,5-dihydrofuran-3-yl)oxy)(hydroxyl)phosphoryl)oxy)propyl)amino)-4-oxobutanoate hydrochloride (I-2)

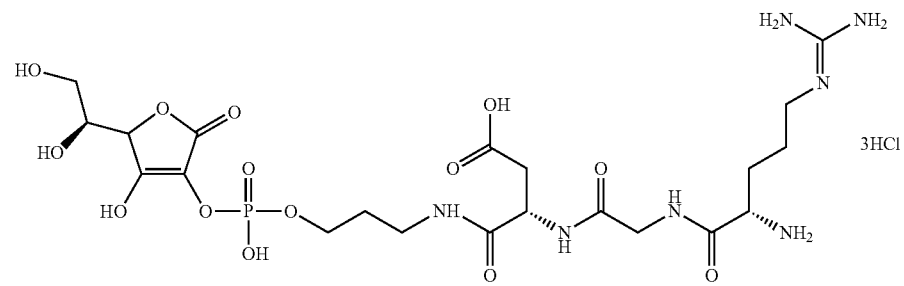 [SMILES: NC(N)=NCCC[C@H](N)C(=O)NCC(=O)N[C@@H](CC(=O)O)C(=O)NCCCOP(=O)(O)OC1=C(O)C([C@@H](O)CO)OC1=O]

The compound IV-2 (2.46 g, 3.5 mmol) in which amino group and carboxyl group are protected obtained in Preparation Example 1-2 was dissolved in dimethylformamide (20 mL), and N,N'-dicyclohexylcarbodiimide (DCC) (0.72 g, 3.5 mmol) and N-hydroxysuccinimide (0.4 g, 3.5 mmol) were added thereto, followed by undergoing the reaction at room temperature for 1 hour. After the reaction, N,N'-dicyclohexylurea produced as a by-product was removed by filtration under reduced pressure. To the resulting filtrate, 3-aminopropyl(5-((S)-1,2-dihydroxyethyl)-4-hydroxy-2-oxo-2,5-dihydrofuran-3-yl)hydrogen phosphate (Vitagen, 1.32 g, 4.2 mmol) of formula II and diisopropylethylamine (1.22 mL, 7.0 mmol) were added and stirred at room temperature for 2 hours. After completion of the reaction, the reaction solution was concentrated under reduced pressure to remove the solvent. The residue was recrystallized by sequential addition of methanol, dichloromethane and isopropyl ether, and filtered to obtain the compound (11S,17S)-t-butyl 6,11-bis((t-butoxycarbonyl)amino)-17-((3-((((5-((S)-1,2-dihydroxyethyl)-4-hydroxy-2-oxo-2,5-dihydrofuran-3 yl)oxy)(hydroxy)phosphoryl)oxy)propyl)carbamoyl)-2,2-dimethyl-4,12,15-trioxo-3-oxa-5,7,13,16-tetraazanonade-6-cen-19-oate) of formula I-2 (3.28 g, 94%) in which amino group and carboxyl group are protected.

ES-MS m/z: 999 [M+H]$^+$

The compound (3.28 g, 3.29 mmol) of formula I-2 in which amino group and carboxyl group are protected was dissolved in 1,4-dioxane (35 mL), and 4 M hydrochloric acid in 1,4-dioxane solution (8.3 mL, 33 mmol) was added thereto, followed by stirring at room temperature for 15 hours. After completion of the reaction, the reaction solution was concentrated under reduced pressure to remove the solvent, and the residue was recrystallized by sequential addition of acetonitrile, dichloromethane and isopropyl ether, and filtered to obtain the title compound (2.25 g, 91%).

ES-MS m/z: 642 [M+H]$^+$ $^1$H NMR (400 MHz, CDCl$_3$) δ 1.28 (t, 1H), 1.62-1.65 (m, 3H), 1.85 (m, 1H), 1.91 (m, 2H), 2.81-2.85 (m, 1H), 2.99-3.04 (m, 1H), 3.17 (m, 2H), 3.20 (m, 2H), 3.40 (m, 1H), 3.45 (m, 2H), 3.63 (s, 1H), 3.85 (m, 1H), 3.91 (m, 1H), 4.13 (m, 1H), 4.76 (m, 1H), 5.24 (m, 1H), 5.85 (m, 1H), 5.82 (m, 1H), 7.71 (m, 2H), 8.67 (m, 1H).

Experimental Example 1: Analysis of Melanin Inhibitory Effect

B16F1 melanoma cell lines (ATCC CRL-6323) were added to a DMEM medium supplemented with 10% fetal bovine serum, 100 U/ml penicillin and 100 μg/ml streptomycin and were cultured under the condition of 37° C. and 5% $CO_2$. After culture, the medium was replaced with DMEM medium (Invitrogen-Gibco-BRL, cells/well), and treated with a suitable amount of a sample solution such that the final concentration of each test compound reached 0 μg/ml, 10 μg/ml, 20 μg/ml or 40 μg/ml. After 72 hours, the medium was removed, and the cells were washed with PBS (phosphate buffered saline), harvested, and dried at 60° C. Next, a melanin extraction solution (1 N NaOH+10% DMSO) was added to the cells which were then lysed at 80° C. Next, the amount of melanin was quantified using synthetic melanin as a standard, and the amount of protein was quantified. The amount of melanin per unit protein was calculated, and expressed as % control value relative to a control.

The results are shown in Table 1 below.

TABLE 1

| Test compounds | Concentration (μg/ml) | Melanin/Protein (μg/mg) | | | | |
|---|---|---|---|---|---|---|
| | | Average | STDEV | EX1 | EX2 | EX3 |
| Control | — | 215.9 | 5.5 | 209.8 | 220.5 | 217.3 |
| KVK-Pal | 10 | 173.3 | 16.1 | 156.9 | 189.1 | 173.8 |
| | 20 | 164.2 | 11.9 | 151.9 | 175.7 | 165.1 |
| LAAP | 10 | 159.9 | 10.2 | 148.2 | 165.8 | 165.8 |
| | 20 | 137.4 | 4.4 | 132.4 | 140.6 | 139.1 |
| Compound I-1 | 10 | 120.9 | 12.2 | 108.6 | 121.0 | 133.0 |
| | 20 | 90.0 | 6.1 | 89.5 | 84.3 | 96.4 |
| Compound I-2 | 10 | 143.4 | 9.3 | 133.4 | 145.1 | 151.7 |
| | 20 | 134.4 | 9.4 | 137.9 | 141.5 | 123.7 |

Experimental Example 2: Analysis of Effect on Collagen Activation

Human neonatal dermal fibroblast cells (Cascade Co.) were seeded into a 24-well microplate (5×10$^4$ cells/well) with DMEM medium supplemented with 10% fetal bovine serum, and were cultured under the condition of 37° C. and 5% $CO_2$ for 24 hours. The medium was replaced with serum-free DMEM medium, and the cells were cultured for 24 hours, and treated with each sample solution such that the final concentration of each test compound reached 1 μg/ml or 5 μg/ml. After 48 hours of culture, the cell culture medium was collected, and the amount of procollagen in the medium was measured using a collagen measurement kit (Takara Shuzo Co., Ltd., Japan). Specifically, the collected cell culture medium was added to a 96-well plate having a primary collagen antibody uniformly applied thereto, and was subjected to an antigen-antibody reaction at 37° C. for 3 hours. The cell culture medium was removed from each well which was then washed four times with PBS. A color-developing substance was added to each well and incubated at room temperature for 15 minutes, and then 1 N sulfuric acid solution was added to each well to stop the reaction. The absorbance at 450 nm was measured with a spectrophotometer. A standard curve was prepared using a standard solution, and the absorbance obtained as described above was substituted into the standard curve to thereby determine the production of procollagen in the cell culture medium in which each test compound was added.

The results are shown in Table 2 below.

TABLE 2

| Test compounds | Concentration (μg/ml) | Procollagen (ng/ml) | | | | |
|---|---|---|---|---|---|---|
| | | Average | STDEV | Ex 1 | Ex 2 | Ex 3 |
| Control | — | 193.9 | 13.6 | 184.1 | 188.2 | 209.5 |
| KVK-Pal | 1 | 244.4 | 17.9 | 248.9 | 259.7 | 224.7 |
| | 5 | 283.6 | 11.0 | 273.9 | 295.5 | 281.3 |
| LAAP | 1 | 242.3 | 10.1 | 231.4 | 251.3 | 244.1 |
| | 5 | 281.1 | 16.1 | 268.1 | 276.1 | 299.1 |
| Compound I-1 | 1 | 277.7 | 13.1 | 278.1 | 264.4 | 290.6 |
| | 5 | 345.7 | 5.9 | 352.4 | 342.1 | 342.5 |
| Compound I-2 | 1 | 253.1 | 9.7 | 252.4 | 243.8 | 263.1 |
| | 5 | 302.7 | 5.3 | 298.1 | 301.6 | 308.5 |

Experimental Example 3: Test for Stability Against Water and Heat

The stability of an active ingredient, which is used in cosmetic compositions, after water and heat, is an important factor not only in a preparation process, but also in the long-term storage of the composition. Thus, the stabilities of compounds I-1 and I-2, prepared in Examples 1 and 2, respectively, against water and heat, were measured. Specifically, each of compounds I-1 and I-2 was stored in a sealed state under the severe conditions of temperature of 40° C. and relative humidity of 75%, and the percentage of the active ingredient in each sample after 3, 7, 14 and 28 days relative to the initial value of the active value of the active ingredient at day 0 was analyzed by high-performance liquid chromatography (HPLC).

The results are shown in Table 3 below.

TABLE 3

| compound (salt) | Day(s) | | | | |
|---|---|---|---|---|---|
| | 0 day | 3 days | 7 days | 14 days | 28 days |
| LAAP (Vitagen) | 100 | 100.4 | 100.9 | 99.9 | 98.5 |
| Compound I-1 | 100 | 101.0 | 100.4 | 99.9 | 99.8 |
| Compound I-2 | 100 | 100.3 | 100.0 | 99.8 | 99.8 |

As can be seen in Table 3 above, each of compounds I-1 and I-2 was tested under severe conditions for 28 days, and as a result, it could be seen that the compounds exhibited excellent stability comparable to that of commercially available LAAP (Vitagen).

Experimental Example 4: Inhibitory Effect Against DNA Methyltransferase (DNMT) Activity In order to examine the mechanism of the effect of compound I-1 on the promotion of procollagen synthesis, the inhibitory effect of the compound against DNMT activity was examined using a nuclear extract isolated from Hela cells and a DNA methyltransferase activity/inhibitor screening assay kit. To a strip coated with cystosine-rich DNA, a Hela cell nuclear extract comprising DNMT, compound I-1, and Adomet, were added. As a positive control, 5-aza-2'-deoxycytidine (5-azadC) was used. A capture antibody, which binds to methylated DNA, and a detection antibody, were sequentially added to the strip, after which a developing solution was added to induce a color developing reaction, and then a stop solution was added to stop the reaction. The absorbance at 450 nm was measured, and based on the measured absorbance, the percent inhibition of DNMT activity was calculated using the following equation 1. The results of the calculation are shown in Table 4 below.

$$\text{Inhibition \%} = [1 - (OD_{inhibitor} - OD_{blank})/(OD_{control} - OD_{block})] \times 100 \quad \text{Equation 1}$$

TABLE 4

| Test compounds | Conc. (µg/ml) | Inhibition % | | | | | | | |
|---|---|---|---|---|---|---|---|---|---|
| | | Average | STDEV | Ex 1 | Ex 2 | Ex 3 | Ex 4 | Ex 5 | Ex 6 |
| 5-azadC | 0.5 | 78% | 16% | 88% | 91% | 60% | 57% | 88% | 85% |
| Compound I-1 | 1 | 40% | 10% | 48% | 48% | 34% | 23% | 40% | 45% |
| | 5 | 52% | 9% | 62% | 60% | 38% | 49% | 52% | 49% |
| | 10 | 70% | 7% | 79% | 79% | 66% | 62% | 65% | 68% |

As can be seen in Table 4 above, compound I-1 inhibited DNA methylation by 50% or more at a concentration of 5 µg/ml or higher, and exhibited the effect of inhibiting DNA methylation in a concentration-dependent manner in the concentration range of 1-10 µg/ml. Thus, it can be seen that compound I-1 has the effect of increasing procollagen level by inhibiting methylation of collagen gene.

Formulation Examples: Cosmetic Compositions Comprising Peptide-Conjugated Ascorbic Acid Derivative Based on the Experimental Examples above, cosmetic compositions comprising the peptide-conjugated ascorbic acid derivative according to the Example of the present invention were prepared according to the compositions shown in Tables below. The following Formulation Examples are for illustrative purposes and are not intended to limit the scope of the present invention.

Formulation Example 1: Preparation of Skin Softener

According to the composition shown in Table 5 below, a skin softener comprising the peptide-conjugated ascorbic acid derivative according to the Example was prepared.

TABLE 5

| Phases | Components | Contents (%) |
|---|---|---|
| Aqueous phase | Purified water | To 100 |
| | Moisturizing component | 10-25 |
| | Thickener | q.s. |
| | Metal ion sequestering agent | q.s. |
| Solubilized phase | PEG-60 hydrogenated castor oil | 0-2 |
| | PEG-40 hydrogenated castor oil | 0-2 |
| | Polyhydric alcohol | 0-10 |
| | Fragrance | q.s. |
| | Ethanol | 0-20 |
| Additional phase I | Dipropylene glycol | 0.23 |
| | Glycerin | 0.02 |
| | *Brassica campestris* sterol | 0.05 |
| | PEG-5 rapeseed sterol | 0.05 |
| | Cholesterol | 0.05 |
| | Ceteth-3 | 0.03 |
| | Ceteth-5 | 0.03 |
| | 1,2-hexanediol | 0.05 |
| | Hydrogenated lecithin | 0.05 |
| | Sodium stearoyl glutamagte | 0.02 |
| | Disodium EDTA | 0.01 |
| | Octyl dodecanol | 0.25 |
| | Purified water | 1.56 |
| | Peptide-conjugated ascorbic acid derivative | 0.10 |
| Additional phase II | Preservative | q.s. |
| | Other additives | q.s. |

Preparation Method (1) Each of the aqueous phase and the solubilized phase was uniformly mixed and dissolved.

(2) The solubilized phase was added to the aqueous phase and mixed to obtain an oil-in-water type emulsion.

(3) Then, the additional phase I solubilized into a phase comprising the peptide-conjugated ascorbic acid derivative dissolved therein was added to and mixed with the emulsion, and then the additional phase II was added to and mixed with the emulsion.

Formulation Example 2: Preparation of Lotion

According to the composition shown in Table 6 below, a lotion comprising the peptide-conjugated ascorbic acid derivative according to the Example was prepared.

TABLE 6

| Phases | Components | Contents (%) |
|---|---|---|
| Aqueous phase | Purified water | To 100 |
| | Ceteareth-6 olivate | 0.1-3 |
| | Moisturizing component | 10-25 |
| | Thickener | q.s. |
| | Metal ion sequestering agent | q.s. |
| Oil phase | PEG-100 stearate | 0.1-1 |
| | Glyceryl stearate | 0.1-1 |
| | Polysorbate 60 | 0.1-1 |
| | Cetyl alcohol | 0.1-1 |
| | Behenyl alcohol | 0.1-1 |
| | Squalane | 5-20 |
| | Tocopheryl acetate | 0.1-0.5 |
| Additional phase I | Dipropylene glycol | 0.23 |
| | Glycerin | 0.02 |
| | Brassica campestris sterol | 0.05 |
| | PEG-5 rapeseed sterol | 0.05 |
| | Cholesterol | 0.05 |
| | Ceteth-3 | 0.03 |
| | Ceteth-5 | 0.03 |
| | 1,2-hexanediol | 0.05 |
| | Hydrogenated lecithin | 0.05 |
| | Sodium stearoyl glutamagte | 0.02 |
| | Disodium EDTA | 0.01 |
| | Octyl dodecanol | 0.25 |
| | Purified water | 1.56 |
| | Peptide-conjugated ascorbic acid derivative | 0.10 |
| Additional phase II | Fragrance | q.s. |
| | Preservative | q.s. |
| | Other additives | q.s. |

Preparation Method (1) Each of the aqueous phase and the oil phase was heated, uniformly mixed and dissolved.

(2) At 75° C., the oil phase was added to and mixed with the aqueous phase to achieve solubilization.

(3) Next, the mixture was cooled to 50° C., and then the additional phase I solubilized into a phase comprising the peptide-conjugated ascorbic acid derivative dissolved therein was added to and mixed with the emulsion, and then the additional phase II was added to and mixed with the emulsion.

Formulation Example 3: Preparation of Cream

According to the composition shown in Table 7 below, a skin lotion comprising the peptide-conjugated ascorbic acid derivative according to the Example was prepared.

TABLE 7

| Phases | Components | Contents (%) |
|---|---|---|
| Aqueous phase | Purified water | To 100 |
| | Moisturizing component | 10-25 |
| | Thickener | q.s. |
| | Metal ion sequestering agent | q.s. |
| Oil phase | PEG-100 stearate | 0.1-2 |
| | Glyceryl stearate | 0.1-2 |
| | Polysorbate 60 | 0.1-2 |
| | Stearic acid | 0.1-2 |
| | Cetearyl alcohol | 0.1-2 |
| | Capric caprylic triglyceride | 10-30 |
| | Tocopheryl acetate | 0.1-0.5 |
| Additional phase I | Dipropylene glycol | 0.23 |
| | Glycerin | 0.02 |
| | Brassica campestris sterol | 0.05 |
| | PEG-5 rapeseed sterol | 0.05 |
| | Cholesterol | 0.05 |
| | Ceteth-3 | 0.03 |
| | Ceteth-5 | 0.03 |
| | 1,2-hexanediol | 0.05 |

TABLE 7-continued

| Phases | Components | Contents (%) |
|---|---|---|
| | Hydrogenated lecithin | 0.05 |
| | Sodium stearoyl glutamagte | 0.02 |
| | Disodium EDTA | 0.01 |
| | Octyl dodecanol | 0.25 |
| | Purified water | 1.56 |
| | Peptide-conjugated ascorbic acid derivative | 0.10 |
| Additional phase II | Fragrance | q.s. |
| | Preservative | q.s. |
| | Other additives | q.s. |

Preparation Method (1) Each of the aqueous phase and the oil phase was heated, uniformly mixed and dissolved.

(2) At 75° C., the oil phase was added to and mixed with the aqueous phase to achieve solubilization.

(3) Next, the mixture was cooled to 50° C., and then the additional phase I solubilized into a phase comprising the peptide-conjugated ascorbic acid derivative dissolved therein was added to and mixed with the emulsion, and then the additional phase II was added to and mixed with the emulsion.

The invention claimed is:

1. A peptide-conjugated ascorbic acid derivative represented by the following formula I or a cosmetically acceptable salt thereof:

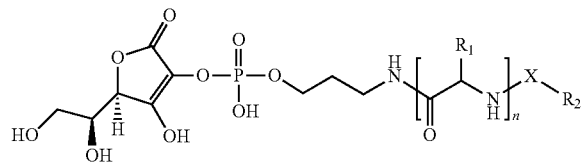

Formula I wherein

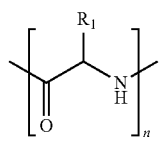

represents a peptide in which the same or different amino acid residues selected from among natural or non-natural amino acid residues are bonded by amide bonds;

$R_1$ represents side chains of the amino acid residues;

X is hydrogen or carbonyl (C=O);

$R_2$ is null when X is hydrogen, or $R_2$ is palmityl, lauryl or stearyl when X is carbonyl; and n is an integer ranging from 2 to 5.

2. The peptide-conjugated ascorbic acid derivative or cosmetically acceptable salt thereof according to claim 1, wherein

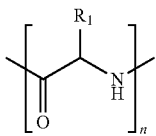

represents a peptide in which the same or different amino acid residues selected from among valine, lysine, glycine, arginine, aspartic acid, threonine and serine are bonded by amide bonds.

3. The peptide-conjugated ascorbic acid derivative or cosmetically acceptable salt thereof according to claim 2, wherein n is an integer ranging from 3 to 5.

4. The peptide-conjugated ascorbic acid derivative or cosmetically acceptable salt thereof according to claim 1, wherein

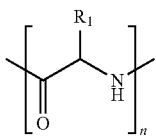

is selected from among lysine-valine-lysine and arginine-glycine-aspartic acid.

5. The peptide-conjugated ascorbic acid derivative or cosmetically acceptable salt thereof according to claim 4, which is selected from among the following compounds:
- (6S,9S,12S)-6,12-bis(4-aminobutyl)-9-isopropyl-5,8,11,14-tetraoxo-4,7,10,13-tetraazanonacosyl (5-((S)-1,2-dihydroxyethyl)-4-hydroxy-2-oxo-2,5-dihydrofuran-3-yl) hydrogen phosphate (I-1); and
- (3S)-3-(2-((S)-2-amino-5-((diaminomethylene)amino)pentanamido)acetamido)-4-((3-(((((5-((S)-1,2-dihydroxyethyl)-4-hydroxy-2-oxo-2,5-dihydrofuran-3-yl)oxy)(hydroxy)phosphoryl)oxy)propyl)amino)-4-oxobutanoic acid (I-2).

6. A method for preparing a peptide-conjugated ascorbic acid derivative represented by formula I, the method comprising a step of subjecting a compound of the following formula II to a condensation reaction with a compound of the following formula IV, and then subjecting a product of the condensation reaction to a deprotection reaction if a protecting group is present in the product:

Formula II

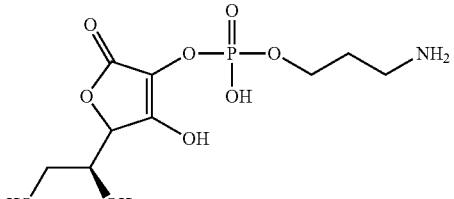

Formula IV

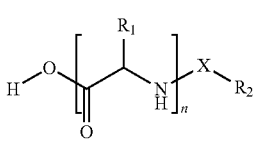

Formula I

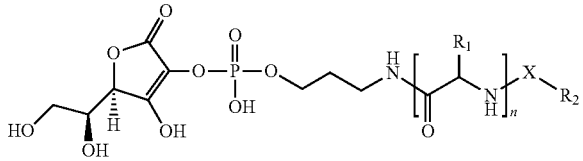

wherein

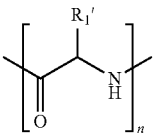

represents a peptide in which the same or different amino acid residues selected from among natural or non-natural amino acid residues are bonded by amide bonds;

$R_1$ represents side chains of the amino acid residues;

$R_1'$ is equal to $R_1$ or is $R_1$ in which amino group or carboxyl group is protected;

X is hydrogen or carbonyl (C=O);

$R_2$ is null when X is hydrogen, or $R_2$ is palmityl, lauryl or stearyl when X is carbonyl;

n is an integer ranging from 2 to 5.

7. A cosmetic composition, comprising (i) a peptide-conjugated ascorbic acid derivative represented by the following formula I or a cosmetically acceptable salt thereof and (ii) cosmetically acceptable base:

Formula I

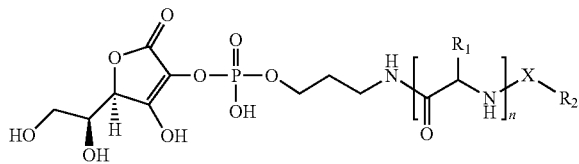

wherein

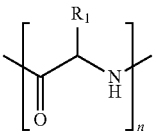

represents a peptide in which the same or different amino acid residues selected from among natural or non-natural amino acid residues are bonded by amide bonds;

$R_1$ represents side chains of the amino acid residues;

X is hydrogen or carbonyl (C=O);

$R_2$ is null when X is hydrogen, or $R_2$ is palmityl, lauryl or stearyl when X is carbonyl; and n is an integer ranging from 2 to 5.

8. The cosmetic composition of claim 7, which is for use of reducing skin wrinkles and whitening the skin.

9. The cosmetic composition of claim 7, wherein the compound of formula I is comprised in an amount of 0.0001 to 2 wt % based on the total weight of the cosmetic composition.

\* \* \* \* \*